United States Patent [19]
Hoffa

[11] 4,227,815
[45] Oct. 14, 1980

[54] MAGNETIC STIRRER FOR SAMPLE CONTAINER OF PHOTOMETRIC ANALYZER

[75] Inventor: Jack L. Hoffa, Brea, Calif.
[73] Assignee: Beckman Instruments, Inc., Fullerton, Calif.
[21] Appl. No.: 55,251
[22] Filed: Jul. 6, 1979
[51] Int. Cl.³ ............................................. G01N 21/01
[52] U.S. Cl. .................................... 356/436; 356/246; 366/273
[58] Field of Search ................................ 356/432–436, 356/442, 426–427, 440, 441, 246; 250/573; 366/273

[56] References Cited
U.S. PATENT DOCUMENTS

| | | | |
|---|---|---|---|
| 3,784,170 | 1/1974 | Petersen et al. | 366/273 |
| 3,981,594 | 9/1976 | George | 356/427 |
| 3,997,272 | 12/1976 | George | 356/427 |
| 4,090,263 | 5/1978 | Hoffa | 366/273 |

*Primary Examiner*—John K. Corbin
*Assistant Examiner*—Bruce Y. Arnold
*Attorney, Agent, or Firm*—R. J. Steinmeyer; Robert R. Meads; John R. Shewmaker

[57] ABSTRACT

Photometric analysis apparatus in which a sample to be optically measured is stirred by a rotating magnetic stirring element within a container holding the sample. An optical path through the container and through the sample therein intersects the rotational path of the stirring element and is hence obstructed by the stirring element in one or more rotational positions. Rotation of the stirring element is controlled in a manner which stops rotation thereof in a position out of the optical path thereby allowing optical measurement of the sample material unobstructed by the stirring element.

4 Claims, 3 Drawing Figures

MAGNETIC STIRRER FOR SAMPLE CONTAINER OF PHOTOMETRIC ANALYZER

BACKGROUND OF THE INVENTION

1. Field of the Invention

The present invention relates generally to the stirring of sample material and, more particularly, to magnetic stirring arrangements for sample containers of photometric analyzers.

2. Description of the Prior Art

Optical assay procedures are being used increasingly in the qualitative and quantitative analysis of clinical or biological fluids such as blood, urine and the like. Typically, a substance to be assayed and one or more reagents are combined and mixed within a light transparent container. The container, in turn, is positioned in a light path of a photometer for assaying the container contents.

The assay of fluids such as blood or serum in the foregoing manner presents a number of practical difficulties which must be overcome to make such approach commercially attractive from a cost, convenience, and reliability standpoint. In this regard only minute quantities of biological fluid may be available for analysis since it is often impossible or unsafe to withdraw more than a few milliliters of fluid from a patient. The difficulty in assaying small volumes is compounded by the typically viscous nature and the often contaminated state of the sample. Thorough mixing of such samples and the various reagents is essential to derive accurate diagnostic information from the assay reaction. Because reagents for biological assays are usually quite expensive, it is essential that the photometric apparatus be of a nature which minimizes the required quantities of sample and reagents without compromising the reliability or accuracy of the assay.

In U.S. Pat. No. 3,784,170 the foregoing assays are performed in a radiation permeable cell positioned in the path of an analytical light beam and containing a magnetic stirring element for stirring the cell contents. The cell is defined by a pair of parallel side walls closed at each end by a pair of opposing end walls to define a sample chamber of generally rectangular cross section. The magnetic stirring element is positioned in the chamber with its magnetic axis parallel to the side walls, and a rotatable drive magnet outside of the cell rotates the stirring element about an axis perpendicular to the side walls so that the plane of rotation of the stirring element is parallel to the side walls. The optical path of the light beam through the cell is specifically disposed above the path of rotation of the magnetic stirring element so that the stirring element cannot obstruct the optical path and interfere with transmission of light through the cell.

A similar arrangement is disclosed in U.S. Pat. No 3,997,272 except that the magnetic stirring element, generally cylindrically configured, is operatively disposed horizontally in the bottom of the cell. This stirring element is only rotated about its own cylindrical axis and hence remains in the same relative horizontal position at all times.

While the approaches in the two aforementioned patents can be employed with some degree of success, they exhibit a number of drawbacks reducing their overall attractiveness. In the former case, displacing the optical axis vertically above and out of the path of rotation of the stirring element increases the required level of solution in the container and hence requires larger volumes of sample and reagent for each assay. In the latter case the operative horizontal orientation of the stirring element would allow the height of the optical path to be lowered thus enabling smaller sample and reagent volumes to be used. However, rotation of the stirring element about its own horizontal longitudinal axis, as opposed to end over end rotation in a vertical plane, provides relatively inefficient and nonuniform stirring of the sample.

SUMMARY OF THE INVENTION

The present invention resides in a new and improved stirring arrangement for a photometric sample container which overcomes the disadvantages of prior arrangements by permitting a reduction in the volume of sample and reagent for performing an assay while retaining a high degree of stirring efficiency. The improved arrangement is achieved in a commercially practical form which is simple and inexpensive in construction and reliable in operation.

To the foregoing ends, the invention contemplates in its broadest aspects photometric analysis apparatus comprising a container for receiving sample material, means establishing an optical path for light to intercept sample material in the container, and means for monitoring light exiting the container along the optical path to measure a characteristic of the sample material together with a magnetic stirring element within the container for stirring sample material therein. Magnetic means coupled to the stirring element rotates the stirring element in a rotational path which intersects and hence obstructs at least a portion of the optical path within the container. Moreover, means is provided for controllably stopping rotation of the stirring element in an orientation out of the optical path thereby allowing optical measurement of the sample material unobstructed by the stirring element. Orienting the optical path and the stirrer rotational path in a common area of the container provides a more compact photometer stirring arrangement which enables the required sample/reagent volume for an assay to be reduced but which retains the superior stirring action of the rotating stirring element for the solution volume which remains.

DESCRIPTION OF THE PREFERRED EMBODIMENT

Figure 3:
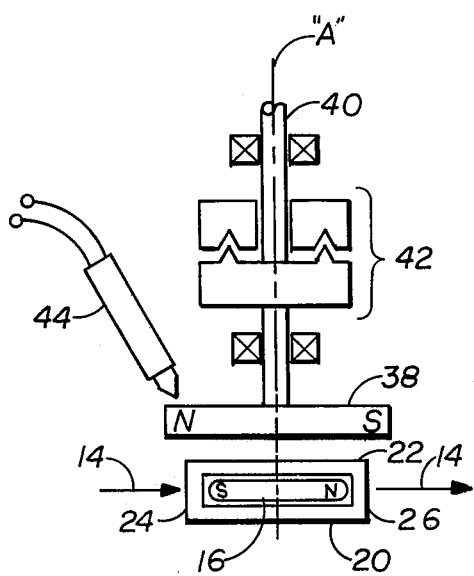
FIG. 3 is a top plan view of the container and stirring arrangement of FIG. 2.

As shown in the drawing for purposes of illustration the present invention is embodied in photometric analysis apparatus 10 comprising a container 12 through which an analytical optical path indicated by arrow 14 passes and a rotatable magnetic stirring element 16 within the container adapted to rotate within the container through a generally circular path 18 which intersects the analytical optical path. Container 12, which corresponds to that in U.S. Pat. No. 3,784,170, is of a generally rectangular configuration and includes closely spaced, parallel side walls 20 and 22 (FIG. 3) connected by opposing parallel end walls 24 and 26. The container includes an open top through which sample may be introduced into the container and a port 28 at its lower end through which reagent is introduced into the container and through which the sample/reagent or other solution is withdrawn from the container. A solution to be assayed is indicated by numeral 30 in the figures.

The photometric analyzer receiving the container 12 is conventional in nature and in its broadest aspect comprises a radiation source 32 and a radiation detector 34. A lens 36 adjacent the source directs radiation therefrom along the analytical optical path 14 through container 12 and through the sample/reagent solution 30 therein to the detector. In the preferred embodiment the optical path 14 traverses the sample container between spaced end walls 24 and 26 but could extend between side walls 20 and 22 if desired. To this end the container, or at least the wall areas for passing radiation, are formed of a suitable radiation permeable material such as quartz, pyrex glass, plastic or other material of known optical characteristics. A typical assay is performed by introducing the components of solution 30 into the container and measuring the change in radiation exiting the container along optical path 14.

The magnetic stirring element 16 is conventional in construction comprising a permanent magnet cylindrical in shape having opposite north-south magnetic poles at its respective ends. Preferably the stirring element is coated with a hydrophobic plastic material in a conventional manner to prevent reaction between the magnet and the sample or reagent within container 12. A conventional drive magnet 38 such as a permanent magnet bar having opposite north-south magnetic poles at its respective ends is positioned outside of container 12 sufficiently close to the container in parallel planar relation to container side walls 20 and 22 as to be magnetically coupled to the stirring element 16 within the container. The drive magnet is connected to the output shaft 40 of a motor (not shown). The output shaft is generally horizontally disposed perpendicular to the container side walls and hence rotates the drive magnet about a horizontal axis "A" in a generally vertical plane of rotation parallel to the side walls of the container. Since the stirring element 16 is magnetically coupled to the drive magnet, the stirring element will be rotated within container 12 through circular path 18 also in a generally vertical plane about a horizontal axis of rotation "B". Axis "A" could be elevated vertically to a level as to be coaxial with axis "B", however axis "A" is preferably oriented slightly below axis "B" for reasons noted subsequently. It will be understood that stirring element 16 need not be a permanent magnet but may simply comprise a material such as iron which can be magnetically coupled to the drive magnet 38.

In accordance with a primary aspect of the present invention the relative orientation of the analytical optical path 14 and the rotational path 18 of stirring element 16 is such that the rotational path intersects at least a portion of the optical path within the container 12. To this end, with rotational path 18 situated near the bottom of container 12, the height of the optical path 14 is established at a relatively low vertical level in the container such that the stirring element intersects and blocks at least a portion of the optical path in one or more of its rotational positions in rotational path 18.

Figure 2:
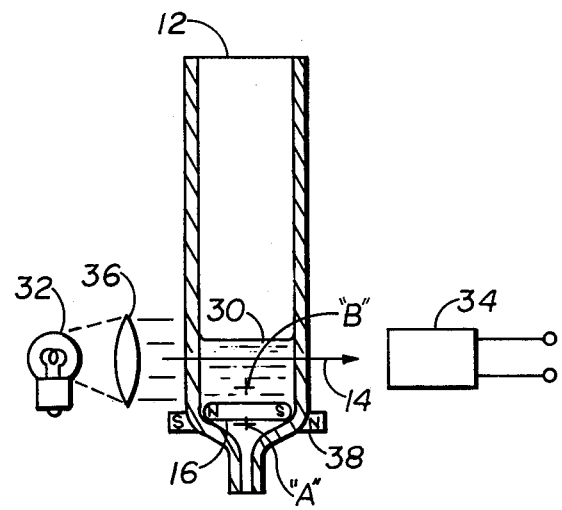
FIG. 2 depicts the photometer similarly to FIG. 1 but with rotation of the magnetic stirring element stopped in accordance with the invention.

In accordance with a further aspect of the invention, means is provided for controllably stopping rotation of the stirring element in an orientation out of the optical path to allow optical measurement of sample at such time with optical path 14 unobstructed by the stirring element. To this end rotation of drive magnet 36 is controlled in a manner to stop in a position which always pulls the stirring element into a stop or rest position out of the optical path. For the illustrated embodiment, a preferred stop or rest position for the stirring element is the generally horizontal position below optical path 14 at the bottom of the container as illustrated in FIG. 2. Various means may be employed for so stopping the drive magnet depending upon factors such as the type of motor employed to rotate the drive magnet, the dimensional constraint of the photometric analysis apparatus, and the like. The motor may be of the free running type in which case a suitably actuated mechanical clutch 42 (FIG. 2) such as a conventional fixed-cog clutch/brake suffices to stop the drive magnet only in either of the two rotational positions in which the drive magnet 38 is horizontal. Alternatively, in digitally controlled systems a conventional pulse operated stepping motor is conveniently used to rotate the drive magnet. In such a system an optical, magnetic, or other conventional shaft rotational position sensor 44, senses a predetermined horizontal rotational position of the drive magnet and generates a feedback control signal for terminating the supply of input pulses to the stepping motor. In such stepping motors, termination of the driving input pulses immediately stops rotation of the motor output shaft, thereby stopping the drive magnet and the stirring element in the horizontal position of FIG. 2.

Figure 1:
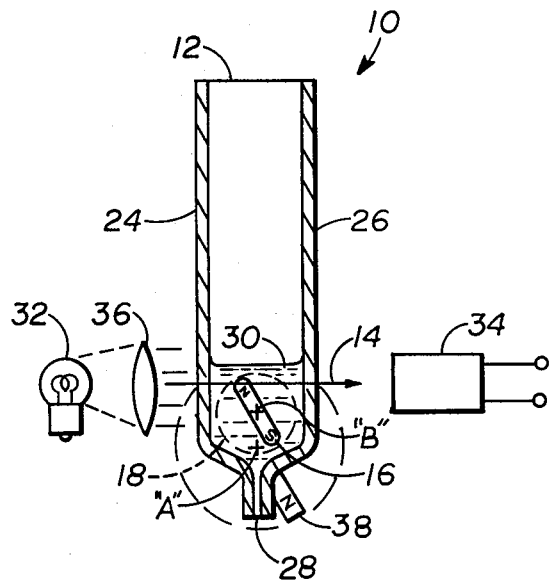
FIG. 1 is a diagrammatic representation of a photometer embodying a sample container and magnetic stirring arrangement of the present invention. The figure illustrates the container in longitudinal sectional in a generally vertical plane.

Controllably stopping rotation of the stirring element 16 in the foregoing manner out of the optical path 14 enables the height of the optical path to be lowered from a position employed heretofore above the rotational path 18 to a position, such as that illustrated in FIG. 1, intercepted by the rotational path thus causing the optical path to be blocked by the stirring element in at least some rotational positions. However, when the stirring element is controllably stopped in an orientation out of the optical path, optical measurements of the sample are then performed in a normal manner by detector 34 with the optical path 14 unobstructed by the stirring element.

With the container 12 configured as shown, detector 34 is adapted to view a cross-sectional area area of the optical path 14 approximately two millimeters by six millimeters with an optical path length of approximately ten millimeters through the container between end walls 24 and 26 and a dimension between side walls 20 and 22 of approximately 2.5 millimeters. With these dimensions a total solution volume 30 of only about 0.25 milliliters is required for an assay compared to a prior requirement of about 0.525 milliliters using the same container. Typically, the reagent is introduced into container 12 through port 28 and the sample is introduced through the upper opening of the container with a pipette or other appropriate sampling devices. The drive magnet 38 and hence the magnetic stirring element 16 are rotated for a period of 2 to 5 seconds or more to thoroughly stir the sample and reagent. After adequate stirring, drive magnet 38 is stopped in the manner previously described in the generally horizontal position of FIG. 2 below the optical path 14. Detector 34 is then employed to measure the radiation exiting the container along the optical path 14 to derive a measure of the sample material.

It has also been discovered that the horizontal axis of rotation "A" of drive magnet 38 can be at a vertical height through container 12 lower than the lowest possible height of horizontal axis of rotation "B" of the stirring element without impairing the rotational efficiency of the stirring element. In other words, though the lowest possible height of axis "B" must allow the ends of the stirring element to clear the bottom surfaces of the container during rotation, the axis of rotation "A" of the drive magnet can be situated below this minimum height of axis "B". This enables the stirring element to be pulled by the drive magnet into the lowest possible horizontal stop or rest position within container 12 below axis "B" as illustrated in FIG. 2. Such enables even further lowering of the height of optical path 14 and consequent reduction in required sample/reagent volumes. For the illustrated embodiment, axes "A" and "B" are vertically spaced about one millimeter from each other.

The present invention enables the height of the optical path 14 to be lowered substantially thereby permitting the level of the column of the sample/reagent solution 30 in container 12 to be correspondingly lowered enabling smaller volumes of reagent and sample to be employed for a particular assay thus effecting cost savings from the reduced sample and reagent quantities heretofore employed. The present apparatus provides this reduced sample/reagent volume while retaining the effective stirring action of a stirring element rotating in a generally vertical plane thereby enabling stirring and measurement to be performed quickly and reliably. Moreover, while a preferred embodiment of the invention has been illustrated and described, it will be apparent that modifications may be made therein without departing from the spirit and scope of the invention as defined by the appended claims.

What is claimed is:

1. In photometric analysis apparatus comprising a container for receiving sample material, means establishing an optical path for light to intercept sample material in the container, and means for monitoring light exiting the container along the optical path to measure a characteristic of the sample material, the improvement characterized by:

a magnetic stirring element within the container for stirring sample material therein;

means magnetically coupled to the stirring element for rotating the stirring element in a rotational path which intersects and hence in which the stirring element obstructs at least a portion of the optical path within the container; and means for controllably stopping rotation of the stirring element in an orientation out of the optical path thereby allowing optical measurement of the sample material unobstructed by the stirring element.

2. The apparatus of claim 1 wherein the container is defined by generally vertically extending walls, the stirring element is rotated about a generally horizontal axis of rotation in a generally vertical rotational path; and the optical path extends generally horizontally through the container at a relative vertical height within the chamber common with the rotational path of the stirring element.

3. The apparatus of claim 2 wherein rotation of the stirring element is stopped with the element in a generally horizontal orientation below the optical path.

4. The apparatus of claim 3 wherein the magnetically coupled means includes means external to the container for generating a magnetic field which rotates about a generally horizontal axis and wherein the horizontal axis of rotation of the magnetic field is situated at a vertical height below the minimum vertical height of the horizontal axis of rotation of the stirring element.

* * * * *